United States Patent [19]

Yount

[11] Patent Number: 5,329,932

[45] Date of Patent: * Jul. 19, 1994

[54] METHODS OF AND APPARATUS FOR MONITORING RESPIRATION AND CONDUCTIVE COMPOSITION USED THEREWITH

[75] Inventor: John E. Yount, Beaverton, Oreg.

[73] Assignee: Oregon Health Sciences University, Portland, Oreg.

[*] Notice: The portion of the term of this patent subsequent to Mar. 31, 2009 has been disclaimed.

[21] Appl. No.: 786,214

[22] Filed: Oct. 31, 1991

Related U.S. Application Data

[63] Continuation-in-part of Ser. No. 433,705, Nov. 9, 1989, Pat. No. 5,099,855.

[51] Int. Cl.$^5$ ............................................. A61B 5/08
[52] U.S. Cl. ............................. 128/721; 128/782
[58] Field of Search .................. 128/721–723, 128/774, 782; 324/691, 699; 338/80, 94, 99, 114, 231

[56] References Cited

U.S. PATENT DOCUMENTS

| | | | |
|---|---|---|---|
| 2,194,809 | 3/1940 | Powell | 128/721 |
| 2,518,906 | 8/1950 | Kocmich | 338/114 |
| 2,671,153 | 3/1954 | Ray et al. | 338/114 |
| 3,268,845 | 8/1966 | Whitmore | 128/721 |
| 3,419,702 | 12/1968 | Piel | 338/114 |
| 3,483,861 | 12/1969 | Tiep | 128/721 |
| 3,520,294 | 7/1970 | Fuzzell et al. | |
| 4,308,872 | 1/1982 | Watson et al. | 128/725 |
| 4,373,534 | 2/1983 | Watson | 128/725 |
| 5,099,855 | 3/1992 | Yount | 128/721 |

FOREIGN PATENT DOCUMENTS 2448339 9/1980 France .

OTHER PUBLICATIONS

Brouillette et al., "Comparison of Respiratory Inductive Plethysmography and Thoracic Impedance for Apnea Monitoring," *Journal of Pediatrics*, Sep. 1987, pp. 377-383.

*Primary Examiner*—Angela D. Sykes
*Attorney, Agent, or Firm*—Millen, White, Zelano, & Branigan

[57] ABSTRACT

An apparatus for measuring respiration includes a first gauge for positioning around a patient's chest and a second gauge for positioning around the patient's abdomen. Each gauge is comprised of a compliant tube, e.g., natural or silicone rubber filled with a conductive gel. The conductive gel is a composition comprising glycerol, water, and, e.g., sodium chloride. Upon securing the gauges about the patient, signals indicative of absolute volume are immediately available, providing a new and improved method of measuring and/or monitoring respiration.

22 Claims, 5 Drawing Sheets

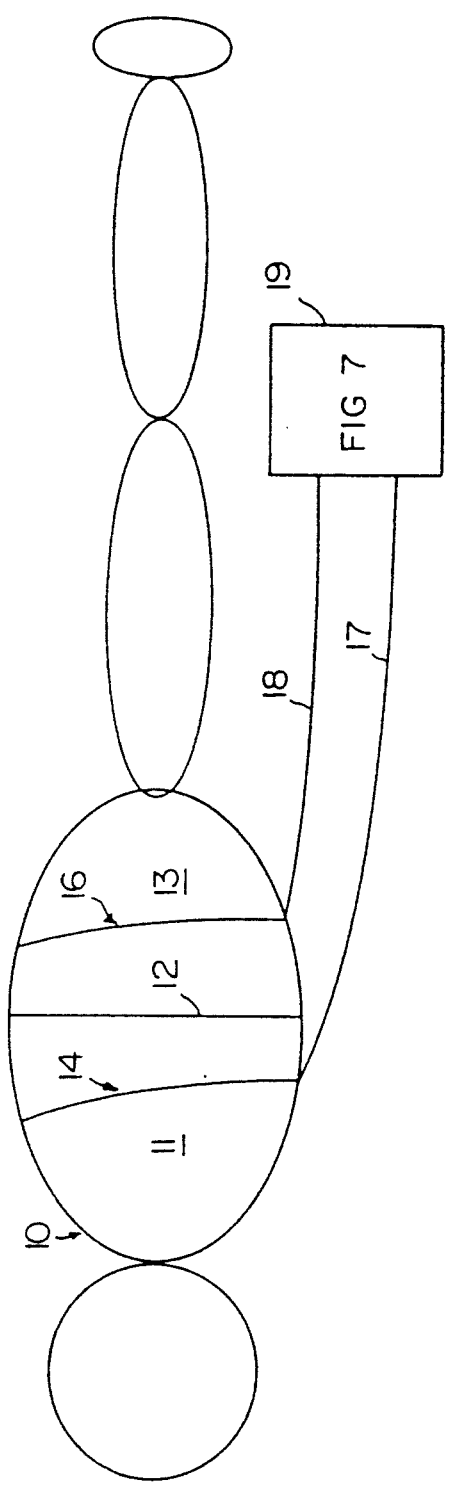
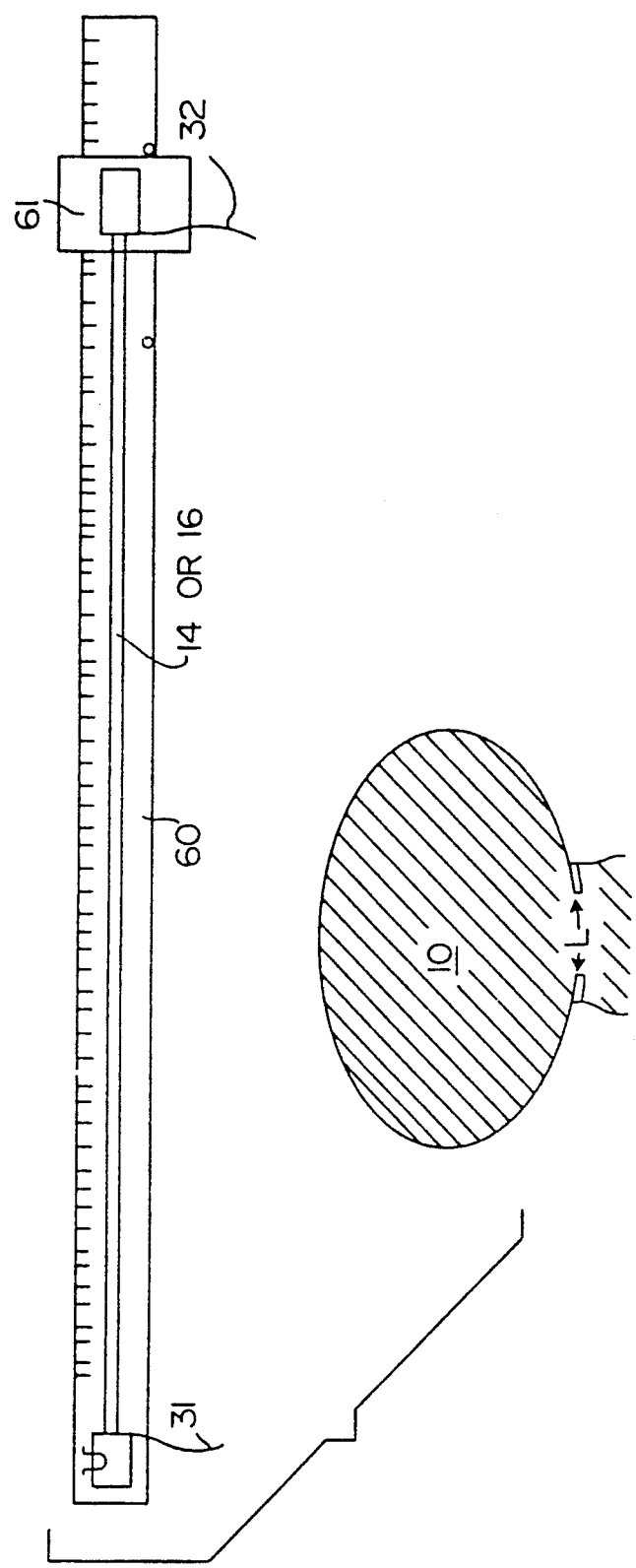
FIG. 1
FIG. 6

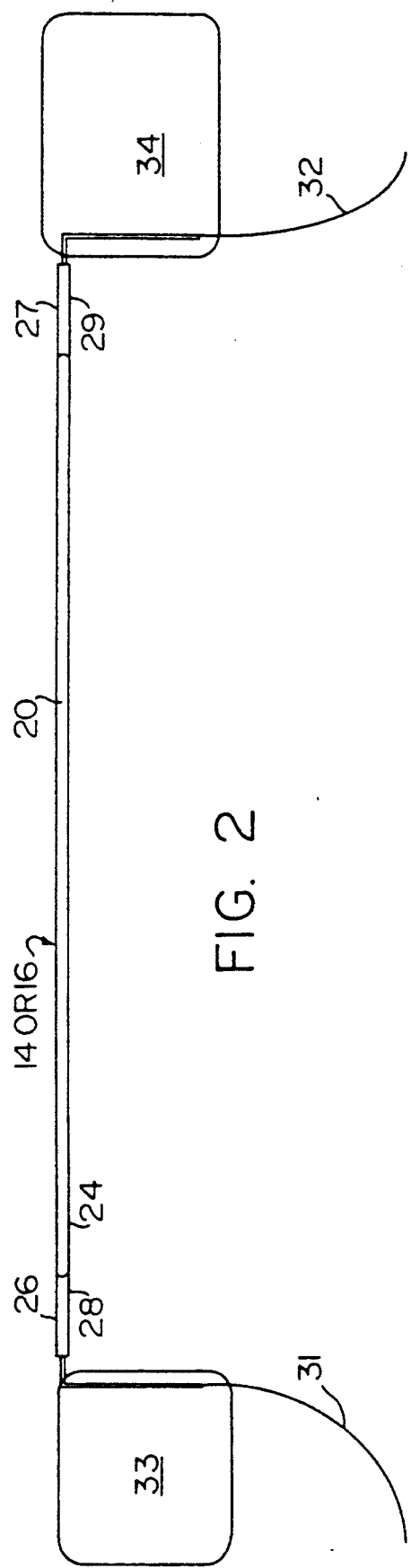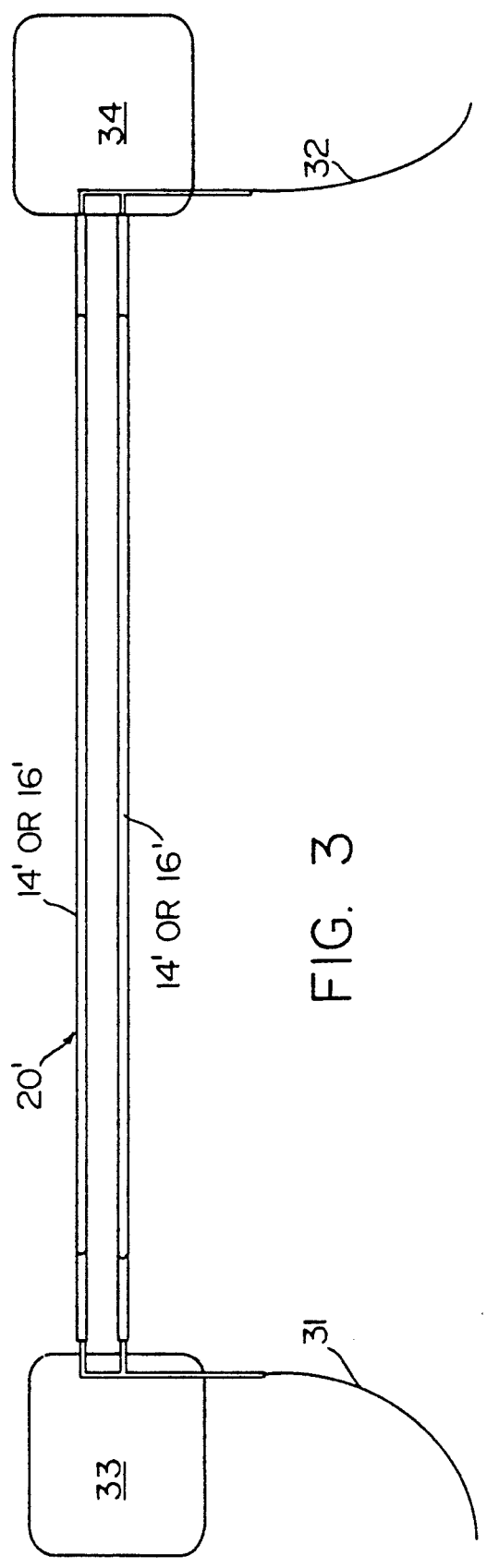

5,329,932

METHODS OF AND APPARATUS FOR MONITORING RESPIRATION AND CONDUCTIVE COMPOSITION USED THEREWITH

CROSS-REFERENCE TO RELATED APPLICATION

This application is a continuation-in-part of U.S. application Ser. No. 07/433,705, filed Nov. 9, 1989, now U.S. Pat. No. 5,099,855 which is entirely incorporated by reference herein.

BACKGROUND OF THE INVENTION

The instant invention relates to apparatus and a process for monitoring respiration as well as to a conductive gel used therewith, wherein the apparatus comprises at least first and preferably second circumferential gauges that attach around a patient's abdomen and chest to monitor expansion thereof as the patient breathes. The gauges are configured as hollow tubes containing the new and improved conductive gel.

In the past, continuous volumetric monitoring of patients' ventilation generally involved use of face masks or mouthpieces, approaches which are not only invasive and uncomfortable to the patient but also interfere with the very breathing patterns being measured. These approaches required considerable cooperation from patients, which cooperation was compromised if the patient was critically ill, comatose, or very young. In addition, leaving mouthpieces in place was a danger in and of itself in that mouthpieces can suffocate patients. Utilizing these invasive methods required constant supervision and attention, further limiting the desirability of these techniques.

In view of such deficiencies, noninvasive techniques were developed such as those exemplified in U.S. Pat. Nos. 3,268,845 and 3,483,861, wherein respiration is monitored by measuring expansion of the patient's torso at primary levels of respiration; namely, expansion of the thoracic cavity, diaphragm, and abdomen. A current approach is shown in U.S. Pat. No. 4,373,534, wherein inductive loops are positioned around the thoracic cavity and abdomen. As the patient breathes, the inductive loops expand and contract, resulting in changes in cross-sectional area and inductance of the loops. Monitoring these changes provides a measure of respiration volume. This has been performed in research for a number of years, using mercury in rubber gauges. The art has continued to progress to current approaches, wherein elastic tubes containing mercury or aqueous solutions are used. Mercury is a material which should, if possible, be avoided since exposure to mercury presents a severe health hazard.

As was pointed out in Brouillette et al., "Comparison of Respiratory Inductive Plethysmography and Thoracic Impedance for Apnea Monitoring," *Journal of Pediatrics*, September 1987, pp. 377–383, incorporated herein by reference, respiratory inductive plethysmographs have advantages over conventional thoracic impedance monitors for infants. Plethysmographs need to be substantially modified before being used for routine monitoring of infants in hospitals or at home. Moreover, the cost is excessive and the associated systems complex.

One approach has been to use natural rubber tubes containing a conductive aqueous solution. However, rubber tubes containing aqueous solutions have been found to have a limited shelf-life of six to ten months and an active life of only 48 hours. Accordingly, they are only useful for overnight diagnostic recordings. Continuous monitoring over several days using such tubes results in considerable expense, since the tubes must be replaced repeatedly. The concept of a rubber tube with an aqueous solution has the advantage of generating very clear signals with low noise generated by physiological and electronic interference. Apparently, the shelf-life of these devices in a Mylar storage envelope and active life after the envelope is opened is limited by passage of the aqueous solution through the walls of the gauge.

Another general deficiency of prior art devices is that these devices are incapable of obtaining rapid, quantitative, absolute measurements which are accurate.

In view of the aforementioned considerations, there is a need for an improved apparatus and method which monitors respiration with accuracy and absolute values, which apparatus has signal-to-noise ratio advantages of currently available natural tubes with aqueous electrolytes, yet have both extended shelf-life and extended active life.

SUMMARY OF THE INVENTION

In the apparatus aspect of the invention, there is provided apparatus for detecting expansion and contraction of a body, comprising:

an elastic tube having first and second sealed ends and containing therein a conductive gel comprising glycerol, water, and at least one conductive salt contained within the tube, which gel changes in inductance as the tube is stretched; and first and second connectors at first and second ends of the tube in electrical contact with the gel, wherein as the tube stretches, changes in the inductance thereof is measured by current flowing between the contacts through the conductive gel.

The instant invention further contemplates a conductive fluid or gel containing water and glycerol, 35–90% by volume and preferably 50–70% by volume and at least one of the following salts: NaCl, preferably from about 20% (g/100 ml) by volume to saturated solution; KCl, preferably from about 20% (g/100 ml) by volume to saturated solution; and sodium or potassium acetate, preferably from about 20% (g/100 ml) by volume to saturated solution; calcium lactate, preferably from about 20% (g/100 ml) by volume to saturated solution; and magnesium sulfate, preferably from about 20% by volume to saturated solution. It is particularly preferred that the salts be present as a saturated solution. The anions of these salts are not critical as long as the overall salt is compatible with the elastic material of the tube. Similarly, the cations are not critical, but the foregoing cations are preferred, other equivalent cations (and salts) being employable. For example, potassium bromide can also be employed (preferably to saturation) due to enhanced conduction characteristics which readily offset its slight toxicity. Thus, the gel will contain water, glycerol at 35–90% by volume and an electrolytic salt as described, preferably as a saturated solution. (Throughout, x % (g/100 ml) by volume refers to x g/100 ml.)

In another aspect of the invention, components can also be added which render the gel and gauge visible to imaging modalities or which enhance such imageability. For example, an iodide salt, e.g., KI or others, can be employed (preferably to saturation) to enhance x-ray imageability, e.g., on a CAT scan. Similarly, an agent enhancing visibility of protons to an MRI (magnetic resonance imaging) scan can be included. Possible candidates are paramagnetic materials such as paramagnetic ion chelates or magnetic particles, etc. (See U.S. Pat. Nos. 4,963,344, 4,731,239 and many others.) The preferred agent is Magnevist ®, Berlex Laboratories, Inc., Wayne, N.J. 07470 (gadopentate dimeglumine). As commercially supplied, the active ingredient is in a solution of 469.01 mg/ml with 0.39 mg/ml meglumine and 0.15 mg/ml diethylenetriaminepentaacetic acid. This commercial formulation can be added to the electrolyte of this invention in a typical ratio of 1 ml of Magnevist ® for 9 ml of electrolyte, thereby producing a concentration of Magnevist ® about 1/10 the commercial levels.

The instant invention further contemplates an apparatus for measuring tidal volume noninvasively by encircling a patient's chest and abdomen with at least one elastic tube, e.g., silicone rubber tube or, preferably, a natural rubber tube, filled with a nontoxic hygroscopic electrolyte. The tube can be fabricated of any equivalently compliant material, e.g., which stretches to provide the physical characteristics described herein. Natural rubber is the preferred compliant material due to the enhanced lifespan of the gauge which ensues.

Each tube has first and second ends sealed with first and second electrical contacts which are in contact with the electrolyte. As the tubes stretch, the impedance of the electrolyte changes. This change in impedance is detected by changes in pulsed current flowing through the electrolyte between the contacts as measured in a constant amperage circuit.

Upon further study of the specification and appended claims, further objects and advantages of this invention will become apparent to those skilled in the art.

BRIEF DESCRIPTION OF THE DRAWINGS

Various other objects, features, and attendant advantages of the present invention will be more fully appreciated as the same becomes better understood when considered in conjunction with the accompanying drawings in which like reference characters designate the same or similar parts throughout the several views, and wherein:

FIG. 1 is a diagram showing attachment of the apparatus of the instant invention to a patient;

FIG. 2 is a planar view of one gauge of the instant invention shown in its relaxed state before being attached to the patient;

FIG. 3 is a planar view of a second embodiment of the gauge having a pair of, e.g., silicone or natural rubber tubes, rather than a single tube;

FIG. 6 is a diagram showing how the tubular gauges of the instant invention are calibrated.

DETAILED DESCRIPTION

Figure 4A:
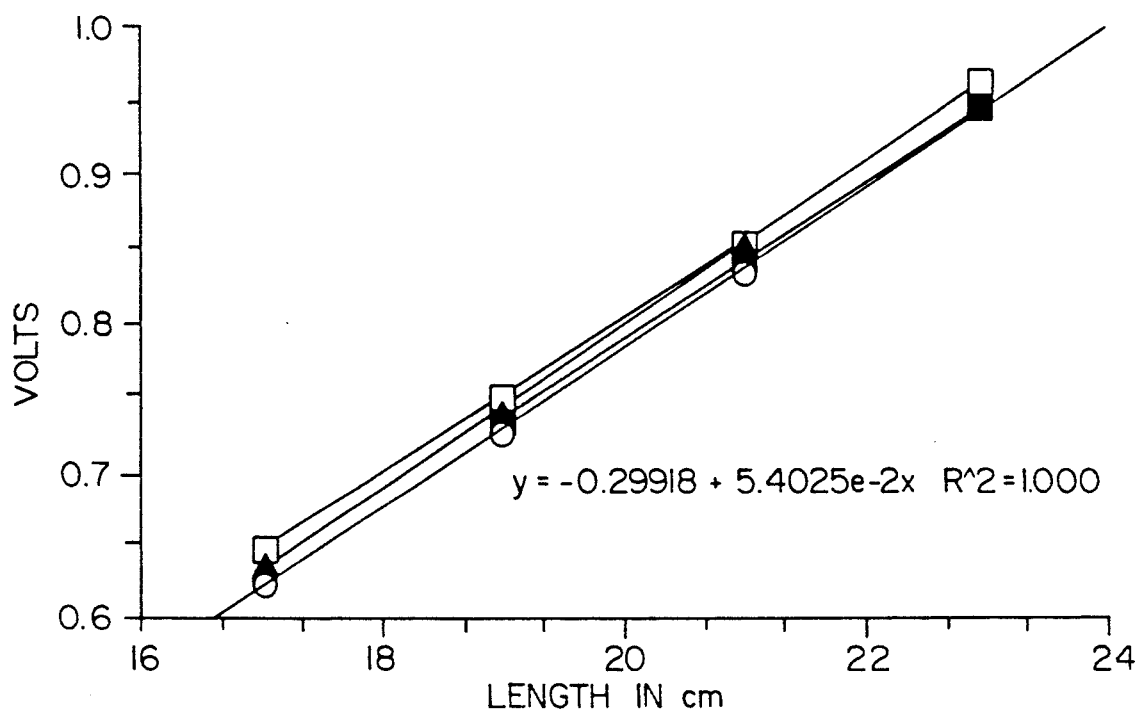
FIGS. 4A and 4B are graphs illustrating change in voltage as a function of tube stretch.

Referring now to FIG. 1, there is shown a patient designated generally by the numeral 10 having a chest or thorax 11, a diaphragm generally illustrated by the numeral 12; and an abdomen 13. A chest gauge, designated generally by the numeral 14, having the configuration of the gauges shown in FIGS. 2 and 3, is tensioned around the patient's chest 11, while an abdominal gauge designated generally by the numeral 16, also having the configuration of the gauges shown in FIGS. 2 and 3 is tensioned around the patient's abdomen In other words, the chest gauge 14 is positioned above the patient's diaphragm 12, while the abdominal gauge 16 is positioned below the patient's diaphragm. The gauges 14 and 16 are connected via leads 17 and 18 to a monitoring circuit, designated generally by the numeral 19 and illustrated more specifically in FIG. 8.

Referring now to FIG. 2, there is shown one embodiment for the gauges 14 or 16, wherein a rubber (e.g., silicone or natural) tube 20 having a length in the range of 16-36 cm, a wall thickness of 0.003", and an inside diameter of 2 mm is filled with a conductive gel 24 so as to have mechanical and electrical characteristics similar to gauges using a mercury conductor. The tube 20 is sealed at first and second ends 26 and 27 by bronze or gold L-shaped contacts 28 and 29, respectively, which are soldered to standard patient lead wire connectors 31 and 32. Velcro TM pads 33 and 34 are bonded or otherwise connected to the L-shaped contacts 28 and 29 so that the gauges 14 and 16 attach securely about the patient's thorax and abdomen.

Referring now to FIG. 3, there is shown an alternative embodiment of the invention, wherein the tubing 20 is arranged in pairs with identical tubes 20A and 20B, each having substantially the same characteristics as the tube 20 of FIG. 2.

Gel 24 is a mixture of the following substances:
glycerol in the range of about 35-90% by volume and preferably about 40-70% by volume mixed with water;
NaCl, from about 20 g per 100 ml by volume to preferably a saturated solution;
KCl, from about 20 g per 100 ml by volume to preferably a saturated solution;
potassium acetate, from about 20 g per 100 ml by volume to preferably a saturated solution;
calcium lactate, from about 20 g per 100 ml by volume to preferably a saturated solution;
magnesium sulfate, from about 20 g per 100 ml by volume to preferably a saturated solution;
optional ingredients: glucose, 1 g to 50 g per 100 ml by volume and commercial, nontoxic food coloring.

A satisfactory method for making the gel is to start with water and to add NaCl to saturation, then add KCl to saturation, potassium acetate to saturation, calcium lactate to saturation, and, if a gel is desired, magnesium sulfate to saturation. In every instance, saturation is observed by the presence of an undissolved solid phase of the added component. Thereafter, the glycerol is added and, after the volume of glycerol exceeds a value of about 40%, undissolved salts surprisingly enter into the solution, thereby resulting in a system having salt concentrations exceeding those in water alone. It is contemplated that other methods may also be used, e.g., adding the salts to a glycerol-water mixture. In any case, an important inventive aspect of this invention is the discovery of the enhanced salt solubilities due to the presence of glycerol, and it is contemplated that equivalent salt mixtures or even single salts may be used to obtain advantages of the invention.

All of the above components are commonly used materials which are available for intravenous fluid preparations and are readily available in sterile form. The solution does not support bacterial growth without glucose. If glucose is included, it is preferred that a mixture be made up in a closed, sterile circuit. Since the mixture is normally a clear gel, the addition of food coloring helps in determining if the contacts are immersed and whether the tube is completely filled with gel so as to preclude air spaces or voids. In addition, since the rubber tubes 14 and 16 have very thin walls, e.g., as low as 0.003 inch, the addition of food coloring indicates whether the walls have been ruptured or whether there has been passage of any of the gel or its constituents through the tubing wall by osmosis. Another advantage of the aforedescribed gel is that it may be stored for an indefinite period without leaking through the tube wall and thereafter serve as a stable transducer for at least a month or more while maintaining impedance below about 80 kohms.

Figure 5:
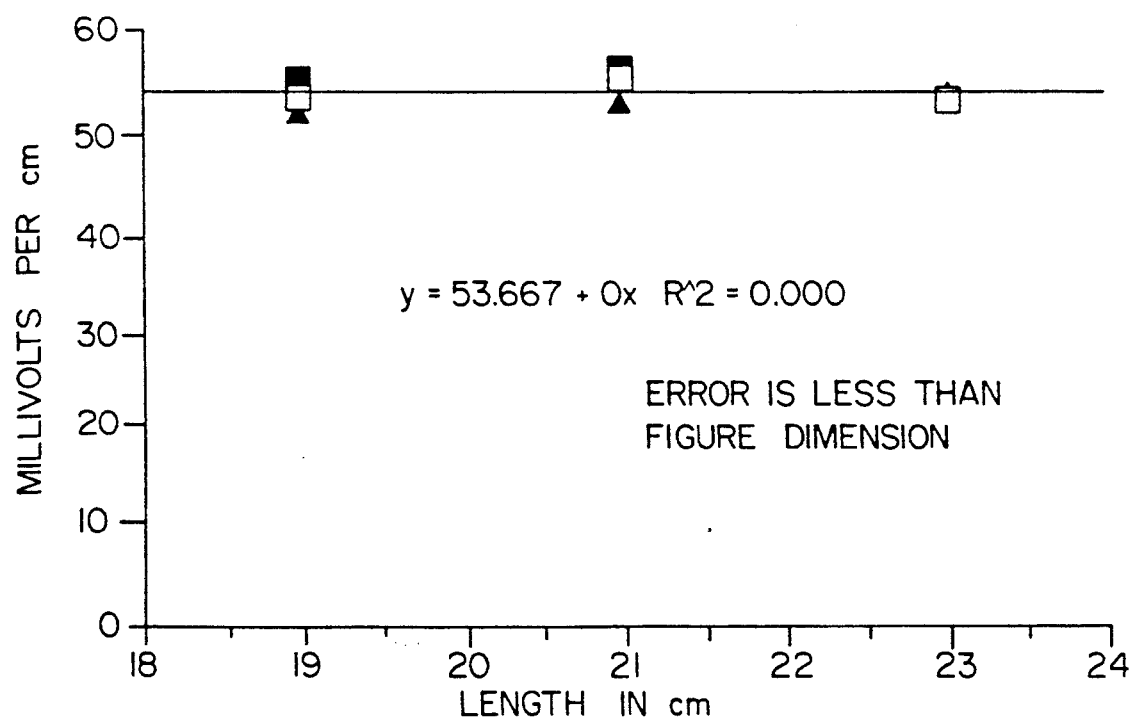
FIG. 5 is a graph illustrating that the voltage rate in millivolts/centimeter remains substantially constant between 18-24 cm when the tube in accordance with the instant invention is in a relaxed state.
Figure 4B:
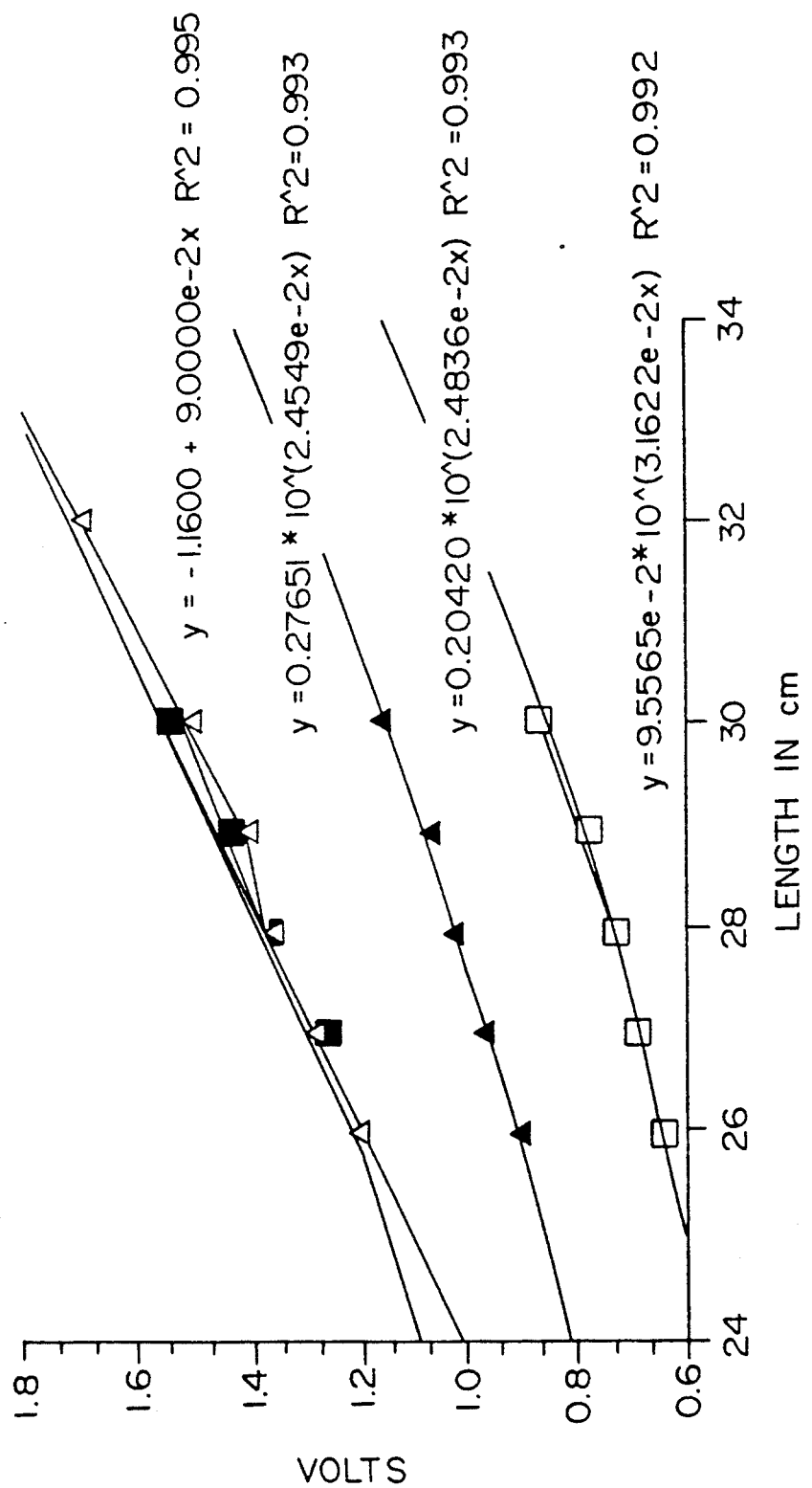

Depending on its geometry, the impedance of the gauges 14 and 16 is in the range of 20–60 kohms, with voltage/centimeter remaining substantially constant at different gauge lengths, as is illustrated in FIG. 5. As is seen by extrapolating FIGS. 4A and 4B, the change in impedance with stretch is nearly linear for at least 50% of the length of the gauge. The signal-to-noise ratio is high, with more than 300 mv/cm of stretch when activated by 2–4 volts applied in the range of 500 Hz to 30 kHz. Gauges 14 and 16 are capable of resolving a 0.1 mm change in dimension with a battery-powered circuit. Since the circumferential respiratory excursion for adults is usually less than 6 cm (0.1 mm to 60 mm), the gauge provides a highly accurate indicator of tidal volume.

By simultaneous cross-sectional measurements of the patient's thorax or chest 11 with the gauge 14 and the patient's abdomen 13 with the gauge 16, approximations of tidal volume accurate to 0.1 mm of gauge length can be obtained. Since the absolute circumference is known, the variation in circumference can be used to estimate volume based on coefficients determined in vivo by one obstruction performed during inspiration and another performed during expiration. The relationship of tidal volume to circumference is a unique coefficient relating volume to the square of the circumference of the applied gauges 14 and 16. The interaction of the thorax 11 and the abdomen 13 is calculated simultaneously in real time to estimate both tidal volume and functional residual capacity. Since the signal from the gauge provides both absolute circumference and circumference variation to an accuracy of 0.1 mm, an estimate of both functional residual capacity and tidal volume can be developed to a presumed accuracy of a few cubic centimeters. By using the two gauges 14 and 16 in fixed geometry around the patient, an independently calibratible monitor for absolute volume of respiratory effort is provided. The gauges 14 and 16 can be manufactured to tolerances where the impedance is calculable simply by knowing the gauge geometry.

Referring now to FIG. 6, there is shown apparatus for performing the calibrating step of the instant invention, wherein gauge 14 or 16 is mounted on an accurate vernier rule 60 by fixing one end 26 thereto and attaching the other end 27 to a sliding element 61 settable to fixed stops. The gauge 14 or 16 is then stretched to measured lengths and the voltage levels indicative of these lengths is entered into the microprocessor 19 (FIGS. 1 and 7) via a standard digital switch.

In order to obtain an accurate average signal, the gauge 14 or 16 may be stretched a number of times between fixed stops and the voltages at those stops entered in and averaged by the microprocessor 9.

The gauge 14 or 16 is then wrapped around a patient 10 and the separation distance "L" entered in the microprocessor 19 as a correction factor via a digital switch. The distance "L" is added to the lengths of the gauges 14 and 16 so that the total circumference of the patient is taken into account when computing residual capacity and tidal volume of the patient's respiration.

By utilizing the aforedescribed gauges 14 and 16, one is able to obtain immediately a reading of absolute volume and need not wait the usual ten minutes for a system using induction loops to average out readings and settle down to a reasonable approximation of volume. Accordingly, the gauges 16 and 17 of the instant invention allow for faster more efficient utilizations of systems such as NMR's and CT's.

Figure 7:
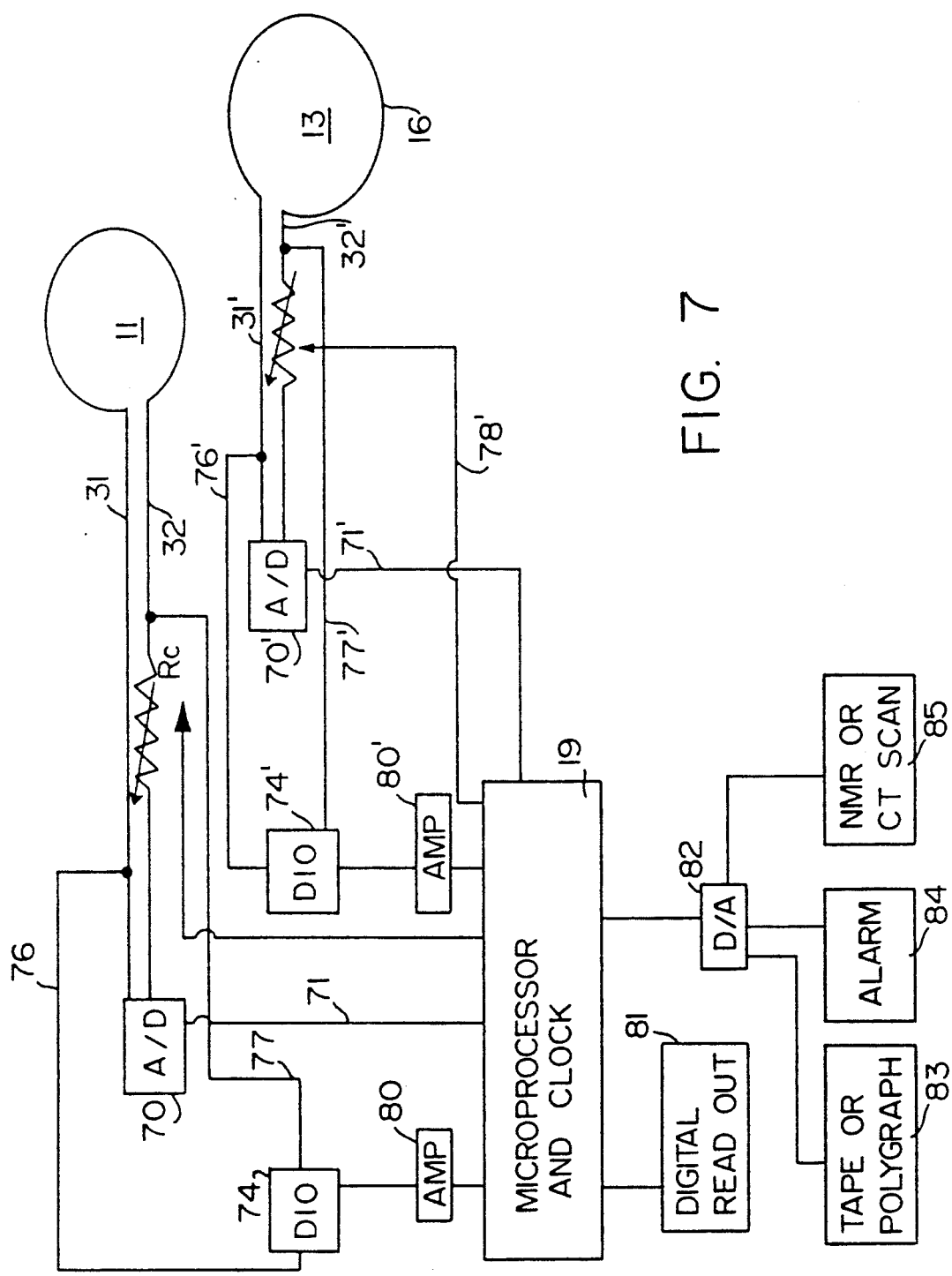
FIG. 7 is a schematic diagram of a circuit for processing information from the tubular gauges shown applied to the patient in FIG. 1.

Referring now to FIG. 7, it is seen that the chest gauge 14 and abdominal gauge 16 are connected to the microprocessor and clock 19. Leads 31 and 31' of the gauges 14 and 16, respectively, are connected through analog-to-digital converters 70 and 70' to the microprocessor and clock 19 via leads 71 and 71'. Leads 32 and 32' are connected to the analog-to-digital converters 70 and 70' via variable resistors Rc and Ra, lines 31 and 31', and 32 and 32' are fed through digital respectively, and their input is also fed to the microprocessor 19 via lines 71 and 71'. The signals on input-output chips 74 and 74' via lines 76 and 76', and 77 and 77', respectively, with the signals on lines 77 and 77' being unmodified by the resistors Rc and Ra in series with the gauges and while changes in pulse amplitude are measured through programmable input amplifiers 80 and 80'.

The output of the microprocessor 19 can be displayed by a digital readout 81, or via a digital-to-analog converter 82, recorded on tape or by a polygraph 83. The signal from the digital-to-analog converter 82 may also sound an alarm 84 or be used to enhance NMR or CT scan images 85.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The entire texts of all applications, patents and publications cited herein are hereby incorporated by reference.

What is claimed is:

1. A stretchable tube comprising a length, wall thickness and inside diameter whereby the tube is useful as a respiratory gauge having minimal response to proximate high frequency electromagnetic fields and containing a composition of 35–90% by volume glycerol, 65–10% by volume water and an amount of a salt in a concentration of from about 20 g per 100 ml to saturated which is effective as an electrolyte, wherein said salt is one of sodium chloride, potassium chloride, potassium acetate, potassium bromide, calcium lactate and a mixture thereof.

2. A tube of claim 1 which is a silicone or natural rubber tube.

3. A tube according to claim 2, wherein all the salts of the composition are present as a saturated solution thereof in a higher concentration than when formulated with water alone.

4. A tube according to claim 2, further comprising a gel-forming concentration of magnesium sulfate.

5. A tube of claim 2, the composition being a fluid.

6. A tube of claim 2, the composition being a gel.

7. A tube of claim 2, wherein the composition further comprises one of an amount of an iodide salt effective to enhance the imageability of the composition to X-rays. An amount of a paramagnetic ion chelate effective to enhance the imageability of the composition to MRI, an amount of a magnetic particle effective to enhance the imageability of the composition to MRI, and a mixture of the X-ray imageability enhancer and at least one of the MRI imageability enhancers.

8. A process for measuring respiration of a patient comprising:
calibrating first and second tubular gauges each comprising a tube of stretchable composition filled with a conductive gel or fluid by stretching the gauges and storing voltage readings indicative of changes in impedance in a microprocessor, and
tensioning the first tubular gauge and securing the tensioned gauge about the patient's chest, tensioning the second tubular gauge and securing the tensioned gauge about the patient's abdomen, and measuring changes in impedance in each gauge as the gauge expands and contracts in length due to respiration of the patient in order to monitor the patient's respiration.

9. A process of claim 8, wherein each tube is a natural rubber tube.

10. The process of claim 9, wherein a measurement of absolute volume of respiratory effort is available immediately because the gauges are calibrated prior to attachment to the patient.

11. An apparatus for monitoring respiration of mammals comprising first tubular gauge means for surrounding the chest of the mammal and second tubular gauge means for surrounding the abdomen of the mammal, each gauge means comprising at least one stretchable tube filled with conductive gel or fluid, the conductive gel or fluid being in electrical contact with a pair of electrical contacts disposed within opposite ends of the at least one tube, means for applying signals indicative of changes in impedance of the at least one tube as the at least one tube stretches to signal processing means wherein immediate, absolute calculation of the thoracic volume is achieved, the at least one tube being of a length and wall thickness and the conductive gel or fluid being of a composition which are each selected to provide a substantially linear change in impedance per unit of stretch.

12. An apparatus of claim 11, wherein the at least one tube is a silicone or natural rubber tube.

13. The apparatus of claim 12, wherein in each case the at least one tube has a length in the range of 16 to 36 cm, a wall thickness in the range of 1 to 6 mills, and an inside diameter in the range of 1 to 3 mm, and wherein the conductive gel within each tube is a composition comprising 35 to 90% by volume glycerol, 65–10% by volume water, and an electrolytic salt in a concentration of from about 20 g per 100 ml to saturation.

14. An apparatus of claim 12, wherein in at least one of said tubes the composition further comprises one of an amount of an iodide salt effective to enhance the imageability of the composition to X-rays, an amount of a paramagnetic ion chelate effective to enhance the imageability of the composition to MRI, an amount of a magnetic particle effective to enhance the imageability of the composition to MRI, and a mixture of the X-ray imageability enhancer and at least one of the MRI imageability enhancers.

15. The apparatus of claim 11, wherein the first and second tubular gauge means each comprise a pair of tubes filled with a conductive gel.

16. The apparatus of claim 15, wherein in each case the at least one tube has a length in the range of 16 to 36 cm, a wall thickness in the range of 1 to 6 mills, and an inside diameter in the range of 1 to 3 mm, and wherein the conductive gel within each tube is a composition comprising 35 to 90% by volume glycerol, 65–10% by volume water, and an electrolytic salt in a concentration of from about 20 g per 100 ml to saturation.

17. An apparatus according to claim 16, wherein the salt in the composition of the tubes is one of sodium chloride, potassium chloride, potassium acetate, potassium bromide, calcium lactate and a mixture thereof.

18. An apparatus for monitoring respiration of mammals comprising first tubular gauge means for surrounding the chest of the mammal and second tubular gauge means for surrounding the abdomen of the mammal, each gauge means comprising at least one stretchable tube filled with conductive gel or fluid, the at least one tube comprising the gauge means each having a length in the range of 16 to 36 cm, a wall thickness in the range of 1 to 6 mills, and an inside diameter in the range of 1 to 3 mm, the conductive gel or fluid within each tube being a composition comprising 35 to 90% by volume glycerol, 65–10% by volume water, and an electrolytic salt in a concentration of from about 20 g per 100 ml to saturation, the conductive gel or fluid being in electrical contact with a pair of electrical contacts disposed within opposite ends of the at least one tube, signal processing means, and means for applying signals indicative of changes in impedance of the at least one tube to said signal processing means wherein immediate, absolute calculation of thoracic volume is achieved.

19. An apparatus of claim 18, wherein the at least one tube is a silicone or natural rubber tube.

20. The apparatus of claim 19, wherein the first and second tubular gauge means each comprise a pair of silicone or natural rubber tubes filled with a conductive gel wherein said salt is one of sodium chloride, potassium chloride, potassium acetate, potassium bromide, calcium lactate and a mixture thereof.

21. The apparatus of claim 20, wherein the composition is about 40% by volume glycerol.

22. An apparatus of claim 20, wherein in at least one of said tubes the composition further comprises one of an amount of an iodide salt effective to enhance the imageability of the composition to X-rays, an amount of a paramagnetic ion chelate effective to enhance the imageability of the composition to MRI, an amount of a magnetic particles effective to enhance the imageability of the composition to MRI, and a mixture of the X-ray imageability enhancer and at least one of the MRI imageability enhancers.

* * * * *